United States Patent [19]

Follet et al.

[11] Patent Number: 4,699,919

[45] Date of Patent: Oct. 13, 1987

[54] LIPOXYGENASE AND CYCLOGENASE INHIBITING THIACHROMEN AND THIEPAN DERIVATIVES AND PHARMACEUTICAL COMPOSITIONS THEREFOR

[75] Inventors: Michel Follet; Marc Bonato, both of Aramon, France

[73] Assignee: Societe de Conseils de Recherches et d'Applications Scientifiques, Paris, France

[21] Appl. No.: 908,407

[22] Filed: Sep. 16, 1986

[30] Foreign Application Priority Data

Sep. 26, 1985 [GB] United Kingdom ................ 8523776

[51] Int. Cl.$^4$ .................... A61K 31/38; C07D 335/06; C07D 337/08
[52] U.S. Cl. ................................. 514/431; 514/432; 549/9; 549/23
[58] Field of Search ...................... 549/9, 23; 514/431, 514/432

[56] References Cited

U.S. PATENT DOCUMENTS 4,436,749 3/1984 Hatinguais et al. .................... 549/9

OTHER PUBLICATIONS

Shen et al, "The Development of Antiasthma Drugs", Part III, ed, D. R. Buckle et al., Butterworth Publishers, Kent, England, 1984.

Primary Examiner—John M. Ford
Assistant Examiner—J. G. Mullins
Attorney, Agent, or Firm—Lucas & Just

[57] ABSTRACT

This invention relates to bicyclic catechol derivatives having the general formulae I and II

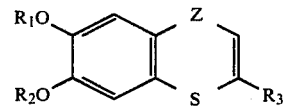

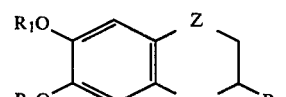

wherein $R_1$, $R_2$, $R_3$ and Z represent various substituents, to a preparation process of the same comprising reacting a compound of formula III

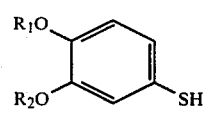

wherein $R_1$ and $R_2$ have the meanings given above with an appropriately substituted propionic or butyric acid (or an ester or a salt of the same) of formula IV

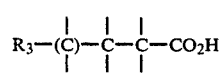

wherein $R_3$ has the meaning given above, and to therapeutical compositions wherein the active ingredient is one of these compounds.

3 Claims, No Drawings

LIPOXYGENASE AND CYCLOGENASE INHIBITING THIACHROMEN AND THIEPAN DERIVATIVES AND PHARMACEUTICAL COMPOSITIONS THEREFOR

The invention relates to bicyclic catechol derivatives, to a process for their preparation and to therapeutical compositions containing the same.

The invention provides the bicyclic catechol derivatives having the general formulae I and II

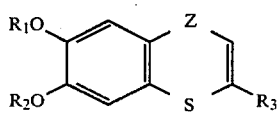

I

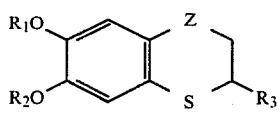

II wherein
each of $R_1$ and $R_2$ independently represents a hydrogen atom or a methyl group;
$R_3$ represents an aromatic radical or a heterocyclic mono or polyunsaturated aromatic radical, optionally substituted by one or more halogen atoms or trifluoromethyl groups and
Z represents a valence bond or a carbonyl, hydroxymethylene, methylene, carbonylmethylene, hydroxyethylene or ethylene group, the oxygen-carbon bond in the case of carbonylmethylene and hydroxyethylene involving the carbon atom adjacent to that involved in ring fusion.

The compounds of the general formulae I and II as above defined are inhibitors of lipoxygenase and cyclogenase. They can be used in human therapy as non steroid antiinflammatory, antithrombotic, antiallergic, antiischemic and antianaphylactic agents.

The invention further provides a process for the preparation of the compounds of the general formulae I and II, the process comprises reacting a compound of formula III

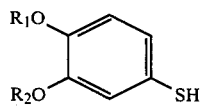

III wherein $R_1$ and $R_2$ have the meanings given above (this compound is prepared by sulphochloration of the aromatic ring according a method derived from that of JUSIUS, LIEBIGS ANN. CHEM 1929, 468, 162, followed by a reduction by nascent hydrogen, —CLEMMENSEN reaction—) with an appropriately substituted propionic or butyric acid (or an ester or a salt of the same) of formula IV

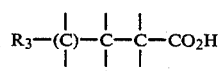

IV wherein $R_3$ has the meaning given above.

In alkaline conditions this gives a compound of formula V

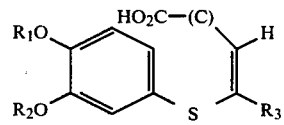

V which is cyclised by dehydrating agents such as phosphoric anhydride, polyphosphoric acids or esters, sulphuric acid, chlorosulphonic acid and other LEWIS acids.

For the compounds of formula II, the process comprises reacting the compound of formula VI with a γ-$R_3$ substituted to γ-butyrolactone VII:

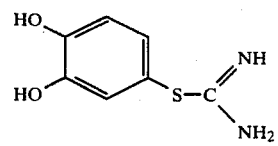

VI

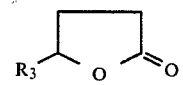

VII according to the method deriving from that one of K. W. BENTLEY and W. I. RUSHVOETH, British Pat. No. 1,428,110, giving the compound of the formula VIII:

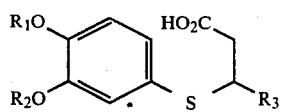

VIII which, after cyclisation on the carboxylic group leads to the desired compound II.

The compounds I and II wherein Z is methylene, ethylene, hydroxymethylene or hydroxyethylene may be obtained by usual methods of reduction.

The carbonyl group might be converted either into a methylene group by treatment by stoichiometric proportions of aluminium trichloride and lithium aluminium hydride according a method deriving from that of H. NAKAZUMI, T. VEYAMA and T. KITAO, J. OF HETEROCYCLIC CHEMISTRY 1984, 21, 193 or by the method of WOLL-KISHNER-HUANG MINLON using hydrazine, or into hydroxymethylene by sodium borohydride reduction according to V. J. TRAYNELIS and R. F. LOVE, J. Org. Chem. 1961 26, 2728.

The invention, finally, relates to pharmaceutical compositions using as an active ingredient therein at least of the compounds as hereinabove defined.

The following examples illustrate the invention.

EXAMPLE 1

6,7-Dihydroxy-2-phenyl-4-oxo-thiachromen (I:$R_1=R_2=H$, Z=CO, $R_3=C_6H_5$)

5 g (0.017 mol) of β-(3,4-dihydroxyphenylthio)-cinnamic acid was added portionwise to 10.5 ml of concentrated sulphuric acid in a two necked 50 ml flask equipped with a magnetic stirrer. The reaction mixture was cooled on ice, and the suspension obtained was dried and then washed with benzene.

Recrystallization from warm ethanol gave an orange powder (yield 13%). This compound has a melting point above 250° C. (Tottoli). Its identity and structure were confirmed by PMR spectroscopy and elemental microanalysis.

|  | C | H |
|---|---|---|
| % Calculated | 66.65 | 3.73 |
| % Found | 66.71 | 3.81 |

EXAMPLE 2

6,7-Dihydroxy-2-(o-trifluoromethyl-phenyl)-4-oxo-thiachromen (I:$R_1=R_2=H$, Z=CO, $R_3=O—CF_3—C_6H_4$)

1 g (0.028 mol) of o-trifluoromethyl-$\beta$-(3,4-dihydroxyphenylthio)-cinnamic acid was dissolved in 15 ml of anhydrous chloroform in a three necked 50 ml flask equipped with a magnetic stirrer and under a light flow of nitrogen. A solution of 3.25 g (0.075 mol) of ethyl polyphosphate in 1 ml of anhydrous chloroform was added at 20° C. The mixture was refluxed for two hours. The reaction mixture was cooled on ice and then made alkaline with ammonia. After extraction, the organic phase washed with water. Evaporation off of the organic solvent gave an orange gum which was purified by silica gel chromatography, eluting with dichloromethane (yield 12%). This compound is a solid melting at 131° C. (Tottoli). Its identity and structure were confirmed by $^{13}$C NMR spectroscopy and elemental microanalysis.

|  | C | H |
|---|---|---|
| % Calculated | 56.80 | 2.70 |
| % Found | 56.64 | 2.69 |

EXAMPLE 3

6,7-Dimethoxy-2-phenyl-4-oxo-thiachromen (I:$R_1=R_2=CH_3$, Z=CO, $R_3=C_6H_5$)

Operating as described in Example 2 but using $\beta$-(3,4-dimethoxyphenylthio)-cinnamic acid in place of o-trifluoromethyl-$\beta$-(3,4-dihydroxyphenylthio)-cinnamic acid, the title compound was obtained in 15% yield. It is a yellow solid melting at 212° C. (Tottoli). Its identity and structure were confirmed by $^{13}$C NMR spectroscopy and elemental microanalysis.

|  | C | H |
|---|---|---|
| % Calculated | 68.44 | 4.73 |
| % Found | 68.44 | 4.74 |

EXAMPLE 4

6,7-Dimethoxy-2-(o-trifluoromethyl-phenyl)-4-oxo-thiachromen (I:$R_1=R_2=CH_3$, Z=CO, $R_3=o—CF_3—C_6H_4$)

Operating as described in Example 2, but using o-trifluoromethyl-$\beta$-(3,4-dimethoxyphenylthio)-cinnamic acid in place of o-trifluoromethyl-$\beta$-(3,4-dihydroxyphenylthio)—cinnamic acid, the title compound was obtained in 50% yield. It is a white solid melting at 194° C. Its identity and structure were confirmed by $^{13}$C NMR spectroscopy and elemental microanalysis.

|  | C | H |
|---|---|---|
| % Calculated | 59.01 | 3.57 |
| % Found | 58.84 | 3.56 |

EXAMPLE 5

7,8-Dimethoxy-2-phenyl-5-oxo-benzo[b] thiepan (II:$R_1=R_2=CH_3$, Z=$CH_2$. CO, $R_3=C_6H_5$)

Operating as described in Example 2, but using 4-phenyl-4-(3,4-dimethoxyphenylthio)-butyric acid in place of o-trifluoromethyl-$\beta$-(3,4-dihydroxyphenylthio)-cinnamic acid, the title compound was obtained 27% yield. Purification was effected by decanting from diethyl ether. This compound is a white solid melting at 135° C. (Tottoli). Its identity and structure were confirmed by $^{13}$C NMR spectroscopy and elemental microanalysis.

|  | C | H |
|---|---|---|
| % Calculated | 68.76 | 5.77 |
| % Found | 68.63 | 5.84 |

EXAMPLE 6

6,7-Dimethoxy-2-(o-trifluoromethylphenyl)-4H-thiachromen (I:$R_1=R_2=CH_3$, Z=$CH_2$, $R_3=o—CF_3—C_6H_4$)

204.9 mg (5.4 mmol) of lithium aluminium hydride and 720 mg (5.6 mmol) of aluminium chloride were dissolved at ambient temperature in 32 ml of anhydrous tetrahydrofuran in a three necked 100 ml flask equipped with a magnetic stirrer and under a light flow of nitrogen. A solution of 1 g (2.7 mmol) of 6,7-dimethoxy-2-(o-trifluoromethyl-phenyl)-4-oxo-thiachromen, prepared as described in Example 4, in 9 ml of anhydrous tetrahydrofuran was added at 25° C. The reaction medium was stirred for 2 hours at 20°-25° C. and then hydrolysed with 0.54 g of water and 1.35 ml of concentrated sulphuric acid. The mixture obtained was filtered and then extracted with diethyl ether. Evaporation off of the organic solvent gave a red powder (yield 20%) melting at 94° C. (Tottoli). The identity and structure of this compound were confirmed by $^{13}$C NMR spectroscopy and elemental microanalysis.

|  | C | H |
|---|---|---|
| % Calculated | 61.36 | 4.29 |
| % Found | 61.52 | 4.35 |

PHARMACOLOGY

Lipoxygenases (LOs) convert arachidonic acid (AA) to hydroxy derivatives and leukotrienes. These products are potent pharmacological agents with potentially important roles in inflammation and hypersensitivity disorders. Several LOs act on AA, principally 5 LO leading to leukotrienes, 12 LO leading to 12-hydroperoxyeicosatetraenoic acid (12 HPETE) and other 12 hydroxy compounds, 15 LO leading to 15 HPETE and other 15 hydroxy compounds, and (at a lower level) 8 LO and 11 LO.

The most important products of LO pathways are leukotrienes produced by 5-LO. The suggested importance of SRS-A in asthma and anaphylactic reactions and the finding that SRS-A belonged to the leukotrienes stimulated the interest in studies of the biological interest of these substances. LTC 4 and LTD 4 (0.1 to 1.nM) caused concentration-dependant contractions of guinea pig ileum as it has been used to determine biological activity of SRS—A relation to histamine. It was found that on a molar basis histamine was 200 times less active than LTC 4, suggesting that 1 unit of SRS-A (6 ng Hist, HCl) corresponds to approximately 0.2 pmole LTC 4. LTC 4 and LTD 4 also increased vascular permeability in guinea pig skin and had smooth-muscle-stimulating properties identical to those previously observed for SRS-A. LTC 4 and LTD 4 play a critical role in cardiac or pulmonary micro-circulation.

LTB 4 influences leukocyte migration by causing leukocyte adhesion to the endothelium in post-capillary venules and by potent chemotactic effects. Therefore leukotrienes are important mediators in host defence mechanisms as immediate hypersensitivity reactions and acute inflammation reactions. Furthermore, the effects of some cyclooxygenase (CO) products and the leukotrienes are complementary. Thus synergism between the leukotrienes causing plasma leakage and the vasodilators PGE 2 and PGI 2 might be of importance in the formation of oedema. Furthermore, a great importance must be given to synergistic effects between the leukotrienes with thromboxane (TxA2) in broncho-constriction. LTC 4 and LTD 4 cause a release of TxA2 in guinea pig lung AS.TxA2 is a potent constrictor of airways, its release might contribute to the broncho-spasm in allergic manifestations. Furthermore, some results seem to demonstrate that some actions of PAF-Acether could be mediated by LTB 4. Non steriodal anti-inflammatory drugs (AINS) do not prevent anaphylaxis. Conversely, they increase hypersensitivity reactions as they mobilize AA for LOs pathways. Corticosteroids (CS) prevent the release of the precursor acting by stimulating the synthesis of lipomodulin a peptid inhibitor of phospholipase A2. By inhibiting the release of AA, CS prevents formation of not only CO products but also LOs products and then leukotrienes formation.

The increased knowledge about the LOs system seems to indicate new possibilities for the development of novel and more therapeutic agents, particularly in diseases related to immediate hypersensitivity reactions such as asthma, allergy, cardiac anaphylaxis, brain ischemia and inflammation. Such drugs might be based on antagonism of end products or inhibition of enzymes involved in the generation and further transformation of the key intermediate LTA 4. A dual effect on the leukotriene pathway and the cyclooxygenase pathway might also be of value.

(1) "In vitro" screening of 7 compounds as potential inhibitors of soybean lipoxygenase a. Introduction Monohydroxy-eicosatetraenoic acids (HETEs) are quantitatively significant metabolites of arachidonic acid (AA) in a variety of mammalian cells and tissues. For example, 12-L-HETE has been identified from the platelets; 5-D-HETE from rabbit PMN; 12-L-HETE, 11-HETE and 15-HETE from guinea pig lung and rat mast cells; and 5-HETE, 8-HETE, 9-HETE, 11-HETE and 12-HETE from human neutrophils. The HETEs distribution is species dependent and representative of AA metabolism catalyzed enzymatically by lipoxygenases. The possible biological roles of these products have not been completely elucidated yet. However, 12-HETE obtained from human platelets showed a chemotactic activity for human polymorphonuclear leucocytes (Siegel, M. I. et al. Proc. Natl. Acad. Sci. 77, 308-312; 1980). 5-HPETE (the hydroperoxy acid) is the precursor of the Slow Reacting Substance, a very potent smooth-muscle contracting agent which mediates symptoms of immediate hypersensitivity. Thus, it appears that inhibition of lipoxygenase could only be beneficial particularly when screening for anti-allergic or anti-inflammatory drugs. Mammalian and plant lipoxygenase (soybean) have many biochemical properties in common, and it has been demonstrated that most inhibitors of the plant enzyme also inhibit lipoxygenases derived from blood platelets or leucocytes (Baumann, J. et al., Prostaglandins 20, 627-639, 1980). Soybean lipoxygenase induces the exclusive formation of 15-HPETE (C.P.A. Van Os et al, Biochim. et Biophys. Acta 663, 177-193, 1981) and has been demonstrated to be ten times more sensitive than platelet lipoxygenase (Wallach, D. P., et al, Biochim. and Biophys. Acta 663, 361-372, 1981). In addition, 15-HETE is a potent and specific inhibitor of platelet lipoxygenase (12-HETE) which indirectly stimulates the formation of thromboxane $A_2$ (Vanderhoek, J., et al., J. Biolog. Chem. 225, 5996-5998; 1980). The 15-hydroperoxy analog has also been reported to suppress pig aortic prostacyclin synthetase activity (Gryglewski, R. J. et al. Prostaglandins 12, 685-713; 1976). This inhibitory action is exerted by the production of a destructive oxidative species probably an OH radical or a species of similar activity (Weiss, S. J., et al. Blood, 53, 1191, 1979).

b. Material and methods (b1) Spectrophotometric Assay

A spectrophotometric method has been developed to determine the enzyme activity according to Corey E. J. et al. (J. Amer. Chem. Soc, 104, 1750-1752; 1982). In a final volume of 1.8 ml was mixed 0.2 M of aerated Borax buffer pH=9.00 with 500 units of soybean lipoxygenase. When inhibitors were tested, they were added in 0.6 ml at final concentrations ranging from $10^{-3}$M to $10^{-8}$M followed by a preincubation of 10 minutes at room temperature. the reaction was initiated by $10^{-4}$M arachidonic acid. Following incubation at room temperature for 90 minutes, 15-HPETE was determined by absorbance measurements at 236 nm.

(b2) Expression of the results

This method was validated with known inhibitors of lipoxygenase. For each test substance a control was included with boiled lipoxygenase in order to take into account any absorption of the compound at the wavelength used. The percentage of enzymatic activity was calculated for each concentration, and the amount of substance required to inhibit 50% of the enzyme activity was calculated by a linear regression on a set of data points describing the log of concentration (M) % inhibition.

c. Results

| Compounds | $IC_{50}$ (Concentration of 50 % inhibition |
| --- | --- |
| Example 1 | $7.25\ 10^{-5}$ |
| Example 2 | $8.23\ 10^{-5}$ |

-continued

| Compounds | IC$_{50}$ (Concentration of 50 % inhibition |
|---|---|
| Example 3 | 1.21 10$^{-6}$ |
| Example 4 | 1.35 10$^{-6}$ |
| Example 5 | 2.29 10$^{-6}$ |
| Example 6 | 1.42 10$^{-6}$ |
| Diphenylthiocarbazone | 1.61 10$^{-6}$ M |

(2) "In vitro" potential inhibition of superoxide anion radical ($O_2^-$)

a. Introduction

The inflammatory process is characterized by a decreased integrity of the endothelial cell barrier, vascular permeability alteration and activation of phagocytic cells such as polymorphonuclear leucocytes (PMN) with the subsequent release and generation into the extracellular space of a group of active compounds, some of which are free radicals. The relationship of these radical species to the other features of inflammation is not completely understood. An essential component of the respiratory burst of activated inflammatory cells such as PMN is the univalent enzymatic reduction of $O_2$ to the superoxide anion radical $O_2^-$. A large proportion of the generated $O_2^-$ is released into the extracellular space where spontaneous dismutation can occur with the concomittant formation of $H_2O_2$ and $O_2$. The simultaneous presence of $O_2^-$, $H_2O_2$ and chelated metal catalysts in the extracellular space can result in further generation of more active oxygen derived molecules such as hydroxyl radical (OH.) and singlet oxygen ($^1O_2$). Superoxide dismutase (SOD) functions as an enzymatic scavenger of $O_2^-$ (McCord et al. J. Biol. Chem. 244, 6049-6055; 1969). whereas 1-methionine and DMSO are both OH. scavenger.

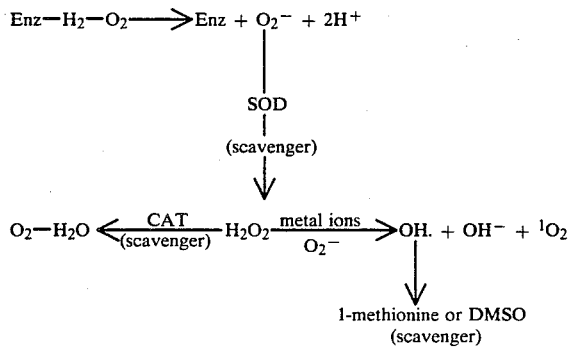

Tentative Mechanism of Substrate-Xanthine Oxidase Free Radical Formation

Scheme 1

The substrate-xanthine oxidase model for the generation of free radicals has been intensively studied (Fridowich, I., J. Biol. Chem. 215, 4053-4057; 1970) and employed to generate free radicals both "in vitro" and "in vivo" (Chmori, H., et al. Biochem. Pharmacol. 27, 1397-1400; 1978).

A convenient and sensitive spectrophotometric assay for specifically detecting and monitoring $O_2^-$ is based on the property of this radical to reduce ferricytochrome C (Cyt $c^{3+}$). The presence of xanthine oxidase with hypoxanthine and Cyt $c^{3+}$ in bicarbonate buffer generates $O_2^-$ which initially reduces Cyt $c^{3+}$ to Cyt $c^{2+}$ (Del Maestro, R. F., Microvascular Res. 22, 255-270; 1981), followed by reoxidation of some Cyt $c^{2+}$ by OH· (Fong, K., et al., Chem. Biol. Interact. 15, 77-89; 1976).

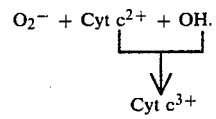

Hydrogen peroxide is formed by the two-electron reduction of molecular oxygen or by the dismutation of $O_2^-$. Catalase (CAT) reduces $H_2O_2$ to $H_2O$.

b. Material and methods

Superoxide Anion Radical $O_2^-$ Generation

The procedure followed was identical to that described by Del Maestro, R. F., J. Bjork and K. E. Arfors (Microvascular Res. 22, 239-254; 1981). Namely the reduction of cytochrome $c^{3+}$ (Cyt $C^{3+}$) was assayed in a system composed of 0.96 mM hypoxanthine, 5.10$^{-5}$M Cyt $c^{3+}$ in bicarbonate buffer pH=7.35 (0.132M NaCl, 4.7.10$^{-3}$M KCl, 2.10$^{-3}$M CaCl$_2$, 1.2.10$^{-3}$M MgSO$_4$, 0.018M NaHCO$_3$). The reaction was started by the addition of xanthine oxidase at a concentration of 0.07 U/ml. The increase in absorbance at 550 nm was monitored at 37° C. in a thermostated spectrophotometric cell every minute for 4 minutes.

Each test compound was added before the xanthine oxidase. A unit of activity was defined as a change of 0.001 units/minute. The percentage of enzymatic activity was calculated for each concentration of tested compounds, and the amount of substance required to inhibit 50% of the enzyme (IC$_{50}$) was calculated by a linear regression on a set of data points describing the log of concentration M/% inhibition.

c. Results

| Compounds | $O_2^-$ Scavenger IC$_{50}$ (Concentration of 50% inhibition |
|---|---|
| Example 1 | 6.64 10$^{-6}$ |
| Example 2 | 6.33 10$^{-6}$ |
| Example 3 | 2.22 10$^{-5}$ |
| Example 4 | 3.67 10$^{-5}$ |
| Example 5 | 5.81 10$^{-6}$ |
| Example 6 | 4.12 10$^{-6}$ |
| Campherol | 9.05 10$^{-6}$ M |
| 3,4-dihydroxy phenylacetic acid | 3.87 10$^{-5}$ M |

(3) "In vitro" screening of compounds on arachidonic cascade metabolism in human platelets microsomes a. Material and methods The enzymatic assay was carried out in silanized glassware according to the procedure of P. Ho, P. Walters and H, Sullivan (Prostaglandins 12, 951; 1976). The reaction mixture containing 50 mM Tris HCl buffer, pH=7.9, 5 mM 2-Tryptophan, 2 M methemoglobin, 0.2 mg of microsomal powder, and the test compound in a total volume of 0.2 ml was incubated at 37° C. for 5 minutes before the addition of 10 μl of 20 μM $^{14}$C arachidonic acid (0.08 μCI). After 5 minutes incubation, the reaction was terminated by the addition of 10 μl of 1 M citric acid.

The mixture was extracted four times with 0.5 ml of anhydrous diethyl ether and dried with sodium sulphate. the residue was resuspended in approximately 40 μl of ether and submitted to chromatography on silica gel plates. The elution system consisted of diethyl ether/methanol/acetic acid (90:1:2). The RF values were measured relative to arachidonic acid. Thin layer chromatography plates (TLC) were exposed on LKB ultrafilm for about 24 hours. Partial identification of the spots were carried out by running standards (PGA$_2$, PGB$_2$, PGE$_2$, PGF$_{2c}$, PXB$_2$, arachidonic acid) in the same solvent system. Quantitative results were obtained by scanning the developed film with a transmission densitometer (EC Apparatus 910) interfaced with a Hewlett Packard 3390A integrator Imidazole and Indomethacin were included as positive standards for specific inhibition of thromboxane synthetase and cyclooxygenase respectively.

b. Cycloxygenase inhibition in human platelets microsomes

|  | IC$_{50}$ (Concentration of 50% inhibition |
|---|---|
| Example 1 | $1.51 \cdot 10^{-4}$ |
| Example 2 | $1.68 \cdot 10^{-4}$ |
| Example 3 | $9.37 \cdot 10^{-4}$ |
| Example 4 | $1.33 \cdot 10^{-5}$ |
| Example 5 | $3.56 \cdot 10^{-6}$ |
| Example 6 | $7.39 \cdot 10^{-6}$ |
| Indomethacin | $1.12 \cdot 10^{-5}$ M |
| Phenylbutazone | $2.74 \cdot 10^{-4}$ M |

The activity of the substances of the cyclooxygenase is quantified by the 2 spots corresponding to PGE$_2$ and TxB$_2$ (ratio PGE$_2$/TxB$_2$).

(4) "In vitro" inhibition of prostaglandin synthetase in ram seminal vesicle microsomes a. Material and methods An improved assay was devised based on the published methods of Baumann et al (Naunyn-Schmiedeberg's Arch. Pharm. 307, 73; 1979) and Takeguchi, C. et al (Biochem. 10, 2372; 1971). The enzymatic radioassay was carried out in silanized glassware. The reaction mixture containing 50 mM Tris HCl buffer, pH=8.3, in the presence of reduced glutathione (GSH), 1 mM, as well as hydroquinone, 0.55 mM, the test compound and 50 μg of ram seminal vesicles microsomal powder in a total volume of 0.2 ml was incubated for 5 minutes at 37° C. before the addition of 10 μl of $^{14}$C arachidonic acid $10^{-6}$M (0.08 μCI). After 30 minutes incubation with occasional shaking, the reaction was terminated by the addition of 10 μl of citric acid 1 M.

The mixture was extracted four times with 0.5 ml anhydrous diethyl ether and dried down with sodium sulphate. The residue was resuspended in approximately 40 μl of ether and submitted to chromatography on silica gel plates. The elution system consisted of diethyl ether/methanol/acetic acid (45:1:2). The RF values were measured in reference to arachidonic acid. Thin layer chromatography plates were exposed on LKB ultrafilm for about 20 hours. Tentative identification of the spots was carried out by running standards (PGE$_1$, PGE$_2$, PGF$_{1a}$, PGF$_{2a}$, PGA$_1$, PGA$_2$, PGB$_1$, PGB$_2$) in the same solvent system. Quantitative results were obtained by densitometry.

b. Results

| Compounds $3.2 \cdot 10^{-6}$ M | Autoradiographes quantification % variation | | |
|---|---|---|---|
|  | PGF$_{2a}$ | PGE$_2$ | PGD$_2$ |
| Example 1 | −51.49 | −15.12 | −5.12 |
| Example 2 | −59.12 | −17.30 | −6.30 |
| Example 3 | −36.26 | −22.47 | −2.11 |
| Example 4 | −42.84 | −41.25 | −11.28 |
| Example 5 | −28.10 | −33.33 | −16.75 |
| Example 6 | −30.29 | −16.48 | −29.63 |
| Phenylbutazone $2 \cdot 10^{-5}$ M | −43.36 | −15.37 | −21.98 |

(5) "In vitro" screening of compounds as potential inhibitors of xanthine oxidase a. Material and methods Xanthine oxidase activity was determined by the method of H. M. Kalckar (J. Biol. Chem. 167, 429–443, 1947) which measures uric acid formation spectrophotometrically.

In a spectrophotometric cuvette, xanthine oxidase was added to give a final concentration of 0.01 units/ml, followed by phosphate buffer 0.05 M, pH=7.4 or the inhibitor. The reaction was started by addition of xanthine at a final concentration of $5 \cdot 10^{-5}$M. The release of uric acid was monitored at 295nm every 30 seconds for 2 minutes (linear phase). A unit of activity was defined as a change of 0.001 units/minute. The percentage of enzymatic activity was calculated for each concentration of tested compounds, and the amount of substance required to inhibit 50% of the enzyme (IC$_{50}$) was calculated by a linear regression on a set of data points describing the log of concentration M as a function of % inhibition.

b. Results

| Compounds | IC$_{50}$ (Concentration of 50% inhibition |
|---|---|
| Example 1 | $5.20 \cdot 10^{-5}$ |
| Example 2 | $5.39 \cdot 10^{-5}$ |
| Example 3 | $1.13 \cdot 10^{-5}$ |
| Example 4 | $9.04 \cdot 10^{-4}$ |
| Example 5 | $3.37 \cdot 10^{-5}$ |
| Example 6 | $1.03 \cdot 10^{-6}$ |
| Folic acid | $6.76 \cdot 10^{-7}$ M |
| Campherol | $7.89 \cdot 10^{-6}$ M |

(6) Inhibition of human leucocytic lipoxygenase (LO)

(a) Inhibition on 5- and 12- lipoxygenases human polynuclear

Protocol for experiment No. 1:

1. Incubation of $15 \times 10^6$ human leucocytes/ml. with Ca$^{2+}$2 mM, Mg$^{2+}$0.5 mM in the presence of the inhibitors at 37° C. for 20 minutes.

2. Stimulation with 1 μg ionophore (A23187)/ml for 4 minutes.

3. Stopping of the incubation with 1 volume of methanol.

4. Analysis by RP-HPLC, colomn C18, 5 μm.

5. Measurement of the height of the peaks and comparison with the internal standard (PGB$_2$).

| Experiment No. 1: Analysis of the results | | | |
|---|---|---|---|
| | IC$_{50}$ | | |
| Products | 5-HETE | LTB$_4$ | 12-HETE |
| Example 1 | $2.10^{-6}$ M | $2.10^{-6}$ M | $2.10^{-6}$ M |
| Example 3 | $10^{-6}$ M | $10^{-6}$ M | $10^{-6}$ M |
| Example 5 | $2.10^{-6}$ | $10^{-6}$ M | $10^{-6}$ M |
| Example 6 | $3.10^{-6}$ | $10^{-6}$ M | $2.10^{-6}$ M |

(b) Inhibition on 5-, 12- and 15- lipoxygenases human polynuclear

Protocol for experiment No. 2:

1. Incubation of $11 \times 10^6$ human leucocytes/ml with the inhibitors for 20 minutes (2 mM Ca$^{2+}$ and 0.5 mM Mg$^{2+}$) at 37° C.
2. Stimulation with 10 μg of arachidonic acid and 1 μg of ionophore (A23187)/ml for 4 minutes.
3. Stopping of the incubation with 1 volume of methanol and analysis by RP-HPLC.
4. Measurement of the height of the peaks and comparison with the internal standard (PGB$_2$).

| Experiment No. 2: Analysis of the results | | | | | |
|---|---|---|---|---|---|
| | IC$_{50}$ | | | | |
| Products | 5-HETE | 12-HETE | 15-HETE | HHT | LTB$_4$ |
| Example 1 | $2.10^{-6}$ M | $10^{-6}$ M | $3.10^{-5}$ M | $4.10^{-5}$ M | $4.10^{-6}$ M |
| Example 2 | $2.10^{-6}$ M | $10^{-6}$ M | $10^{-5}$ M | $5.10^{-5}$ M | $2.10^{-6}$ M |
| Example 3 | $5.10^{-5}$ M | $5.10^{-6}$ M | $5.10^{-5}$ M | $10^{-6}$ M | $5.10^{-6}$ M |
| Example 4 | $10^{-6}$ M | $10^{-5}$ M | $2.10^{-6}$ M | $10^{-5}$ M | $5.10^{-6}$ M |
| Example 5 | $3.10^{-6}$ M | $2.10^{-6}$ M | $10^{-6}$ M | $2.10^{-6}$ M | $10^{-6}$ M |
| Example 6 | $2.10^{-6}$ | $3.10^{-6}$ M | $5.10^{-6}$ M | $2.10^{-6}$ M | $10^{-6}$ M |

Remarks

Stimulation of the 15-lipoxygenase by the above three compounds, at concentrations of $10^{-6}$M to $3 \times 10^{-6}$M is noted, whereas the 5-lipoxygenase is inhibited at these concentrations.

It will be noted that in experiment No. 1, the leucocytes have been stimulated by the ionophore along whereas in experiment No. 2, the cells have been stimulated with ionophore and arachidonic acid. The presence of the arachidonic acid exogene augments by 10 times the ID$_{50}$ of the inhibitors; on the other hand, the addition of the arachidonic acid allows measurement of the activity of 15-lipoxygenase, normally not detectable in leucocytes stimulated by ionophore alone.

We claim:

1. A bicyclic catechol derivative selected from the group consisting of:

6,7-Dihydroxy-2-phenyl-4-oxo-thiachromen;

6,7-Dihydroxy-2-(o-trifluoromethyl-phenyl)-4-oxo-thiachromen;

6,7-Dimethoxy-2-phenyl-4-oxo-thiachromen;

6,7-Dimethoxy-2-(o-trifluoromethyl-phenyl)-4-oxo-thiachromen;

7,8-Dimethoxy-2-phenyl-5-oxo-benzo [b] thiepan; and 6,7-Dimethoxy-2-(o-trifluoromethylphenyl)-4H-thiachromen.

2. A pharmaceutical composition comprising a pharmaceutically acceptable carrier and a lipoxygenase-inhibiting amount of bicyclic catechol derivative as set forth in claim 1.

3. A pharmaceutical composition comprising a pharmaceutically acceptable carrier and a cyclogenase-inhibiting amount of bicyclic catechol derivative as set forth in claim 1.

* * * * *